US006207695B1

(12) United States Patent
Nelson et al.

(10) Patent No.: US 6,207,695 B1
(45) Date of Patent: Mar. 27, 2001

(54) CHIRAL IMIDAZOLE FUNGICIDAL COMPOSITIONS AND METHODS FOR THEIR USE

(75) Inventors: Richard A. Nelson, Pittstown; Norman W. Thomas, Warren; George W. Matcham, Flemington, all of NJ (US); Sue L. Lin, Levittown, PA (US); Minghua Zhang, Edison; Craig M. Lewis, East Brunswick, both of NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 09/469,432

(22) Filed: Dec. 23, 1999

Related U.S. Application Data

(60) Provisional application No. 60/114,508, filed on Dec. 31, 1998.

(51) Int. Cl.⁷ .................................................. A01N 43/50
(52) U.S. Cl. .............................................................. 514/399
(58) Field of Search ................................................ 514/399

(56) References Cited

U.S. PATENT DOCUMENTS 3,658,813    4/1972    Godefroi et al. .................... 260/240

OTHER PUBLICATIONS

Tanaka et al, Int. Symp. Chromatogr. (1995) pp. 395–400.*
Tomlin, The Pesticide Manual Incorporating The Agrochemicals Handbook, 10ᵗʰ Ed. (1995) pp. 580–581.*
Tanaka et al, Int. Symp. Chromatogr. (1995), pp. 395–400 Abstract only.*
Cremlyn, R.J., *Agrochemicals*, John Wiley & Sons (eds.), 1991, 157–216.
Srebnik, M. et al., *J. Org. Chem.*, 1988, 53, 2916.
Tomlin, C. (ed.), "The Pesticide Manual Incorporating the Agrochemicals Handbook," *Royal Society of Chemistry, 10ᵗʰ Edition*, 1995, 580–581.

* cited by examiner

*Primary Examiner*—Allen J. Robinson
(74) *Attorney, Agent, or Firm*—Woodcock Washburn Kurtz Mackiewicz & Norris LLP

(57) ABSTRACT

Chiral fungicides and compositions containing the same are provided. Also provided are methods for using the compositions of the present invention for inhibiting the growth of fungi, including phytotoxic fungi. The use of a single isomer in treating particular plant species and against particular fungi allows for selective inhibition of fungal growth with reduced fungicidal phytotoxic effects.

11 Claims, No Drawings

CHIRAL IMIDAZOLE FUNGICIDAL COMPOSITIONS AND METHODS FOR THEIR USE

This Application claims benefit of U.S. provisional Application Ser. No. 60/114,508 filed Dec. 31, 1998.

FIELD OF THE INVENTION

The present invention relates to chiral fungicidal compositions, and to methods for using the chiral fungicidal compositions to prevent and treat fungal diseases in plants, including the seeds of plants and in plant produce and crops.

BACKGROUND OF THE INVENTION

Fungicides have well-known commercial value in protecting desirable plants from the development of fungal diseases. However, fungicides can be toxic to the plants to which they are applied as well as to beneficial organisms. Thus, it is desirable to maximize the efficacy of fungicides in order to minimize such detrimental effects on plants.

A wide variety of chemical compounds, differing in chemical structure, mechanism of activity, and preferred mode of application, are useful as fungicides. Exemplary types of chemical compounds useful as fungicides include chlorobenzenes and related compounds, quinones, dicarboximides, and systemic fungicides including sulphonamides, benzimidazoles, thiophanates, aminopyrimidines, piperazines, pyridines, imidazoles, and triazoles. These and other fungicidal compounds are described in R. J. Cremlyn, *Agrochemicals,* pp. 157–216, John Wiley & Sons, New York, N.Y. (1991).

The fungicide 1-[2-(2,4-dichlorophenyl)-2-(2-propenyloxy)ethyl]-1H-imidazole, known as Imazalil, is an imidazole fungicide. It is used, for example, to control powdery mildews in cucumbers, marrows and ornamentals, and Fusarium in seed potatoes. It is also used as a seed dressing for control of diseases in cereals such as, for example, Fusarium and Helminthosporium spp. Imazalil is also active against storage diseases, such as, for example, Penicillium, Gloeosporium, Phomopsis, and Phoma spp., of citrus fruit, pome fruit, bananas, and seed potatoes. Furthermore, Imazalil is active against benzimidazole-resistant strains of plant pathogenic fungi (*The Pesticide Manual,* Datix International Ltd., Bungay, Suffolk, The Bath Press, Bath, 1995).

Imazalil is presently used in its racemic form, and there is heretofore no reported use of a single enantiomer of Imazalil as a fungicide and no suggestion for such use. There remains a need for more highly effective fungicides with an improved balance between fungitoxicity and phytotoxicity. It is also desirable to reduce the costs associated with the use of fungicides. The present invention is directed to these, as well as other, important ends.

SUMMARY OF THE INVENTION

One embodiment of the present invention provides a method for inhibiting the growth of fungus on a plant comprising applying to the locus of the plant a fungicidally effective amount of the (S)-enantiomer of 1-[2-(2,4-dichlorophenyl)-2-(2-propenyloxy)ethyl]-1H-imidazole, substantially free of the (R)-enantiomer.

In another embodiment of the present invention a fungicidal composition comprises the (S)-enantiomer of 1-[2-(2,4-dichlorophenyl)-2-(propenyloxy)ethyl]-1H-imidazole, substantially free of the (R)-enantiomer, and an agriculturally acceptable carrier.

In certain preferred embodiments, the amount of the (S)-enantiomer is at least about 90% by weight of the 1-[2-(2,4-dichlorophenyl)-2-(2-propenyloxy)ethyl]-1H-imidazole present in a fungicidal composition, based on the total weight of active ingredient in the fungicidal composition.

The present invention provides an effective method for controlling and/or inhibiting the growth of fungi in association with plants. As used herein, fungi "in association with" include fungi on or in a plant, on plant seeds, on crops or on plant produce. Such fungi which interfere with the growth, development, or reproduction of a plant are also comprehended hereby. The invention also provides new and effective fungicidal compositions for use in preventing and controlling fungal diseases in plants, seeds, produce, etc. These as well as other aspects of the present invention are described in more detail below.

The present invention is directed to chiral fungicidal compositions, and to methods for using the chiral fungicidal compositions to prevent and treat fungal diseases in plants including the seeds of plants and in plant produce and crops. In some preferred embodiments, the chiral fungicidal compositions comprise 1-[2-(2,4-dichlorophenyl)-2-(2-propenyloxy)ethyl]-1H-imidazole, also known, and referred to alternately herein, as Imazalil.

DETAILED DESCRIPTION OF PREFERRED EMBODIMENTS

In accordance with the present invention, there are provided chiral fungicidal compounds having formula (I):

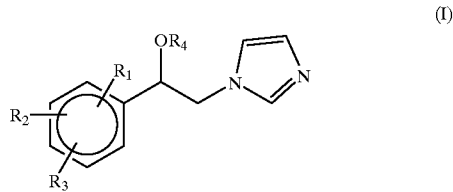

(I)

wherein: $R_1$, $R_2$, and $R_3$ are, independently, H, F, Cl, Br, I, OH, SH, $NH_2$, or $NO_2$; $R_4$ is $C_1$–$C_6$ alkyl, $C_1$–$C_6$ alkenyl, $C_1$–$C_6$ alkynyl, or allyl, and agriculturally acceptable salts thereof, enriched in the (S)-enantiomer and, preferably substantially free of the (R)-enantiomer.

The present invention also provides compositions in which at least about 70% by weight, (which is also, in this case, mole percent) based on the total weight of active ingredient in the composition, is present as the (S)-enantiomer. It is preferred that at least about 80 percent by weight of the (S)-enantiomer is present in the compositions of the present invention. More preferably at least about 85 percent by weight of the (S)-enantiomer is present. Still more preferably at least about 90 percent, even more preferably at least about 95 percent, and still more preferably at least about 99 percent of the (S)-enantiomer is present in the compositions of the present invention. "Active ingredient", as used herein, refers to fungicidally active compounds and can include one or more other fungicidal or other active compounds known in the art. It is preferred that at least one of $R_1$, $R_2$, $R_3$ be a halogen, preferably Cl. It is also preferred that the phenyl moiety be 2,4-dichloro. $R_4$ is preferably allyl. In highly preferred embodiments of the present invention, the compound is (S)-1-[2-(2,4-dichlorophenyl)-2-(propenyloxy)ethyl]1H-imidazole, also referred to as (S)-Imazalil.

The (R)- and (S)-enantiomers of Imazalil were synthesized by stereospecific synthesis from (R)-2-chloro-1-(2',4'-dichlorophenyl)-1-ethanol and (S)-2-chloro-1-(2',4'-dichlorophenyl)-1-ethanol, respectively. The enantiomeric purity of these compounds was determined by chiral derivatization and GC analysis of the halohydrin intermediates. Mosher's Acid Chloride ($\alpha$-methoxy-$\alpha$-trifluoromethylphenylacetyl chloride), is a well-known chiral derivatizing agent. It has been successfully employed for the derivatization and chiral analyses of a number of alcohols and amines. It is commercially available in both enantiomeric forms and does not require any additional reagents for the derivatizations when purchased in the acid chloride form. Mosher's Acid Chloride exhibits marked stability toward racemization even under severe conditions of acidity, basicity, and temperature. Another advantage of using Mosher's Acid derivatives for chiral analyses are their inherent volatility, which allows lower molecular weight derivatives to be analyzed by gas chromatography. Mosher's Acid Chloride has been used as a derivatizing agent for the chiral analysis of the reduction product of 2,2',4'-trichloroacetophenone with diisopinocampheylchloroborane (DIP-Cl). Brown et al., *J. Org. Chem.*, 1988, 53, 2916. After derivatization, diastereomeric Mosher's esters were analyzed on a Supelcowax glass capillary GC column for the direct determination of enantiomeric excess.

The present invention also provides methods for inhibiting the growth of one or more species of fungi on or in a plant. Such methods include application of a fungicidally effective amount of a composition of the present invention to the locus of the plant. "Inhibition" of the growth of fungi, as used herein, is intended to include prevention of growth, halting of growth, slowing of growth, and/or killing of one or more species of fungi. Thus, the fungicidal method of the invention includes preventative, protective, prophylactic, systemic and eradicative treatments. The term "plant", as used herein, includes seeds, seedlings, bushes and trees. This term also includes fruits and vegetables that have been harvested, i.e., fruits in the post-harvest stage and grains and vegetables.

Compositions of the present invention are useful for inhibiting the growth of fungi, including phytotoxic fungi. It has been surprisingly and unexpectedly discovered that the application of the (S)-enantiomer of the subject compounds provides increased effectiveness against the growth of fungi, which is in some cases above the expected two-fold increase that would occur merely by replacing the less effective enantiomer with the same quantity of the more active one. For example, when tested against *Aspergillus nidulans* on dextrose agar plates, 0.5 microgram ($\mu$g) of the (S)-enantiomer alone inhibits growth of the fungus in a zone of equivalent diameter to the inhibition zone observed when 5 $\mu$g of the (R)-enantiomer is applied. Thus, ten times the quantity of the (R)-enantiomer is required to obtain the same degree of inhibition of growth of *Aspergillus nidulans* as obtained with the (S)-enantiomer.

As an example of effectiveness of the compounds against phytotoxic fungi, the (S)-enantiomer of Imazalil provided 86.6% control of powdery mildew (*Erysiphe graminis*) when applied at a rate of 38.4 ppm, in contrast with only 23.3% control by the (R)-enantiomer applied at a rate of 58 ppm. At an application rate of 76.8 ppm, the (S)-enantiomer provided 99.3% control of powder mildew, while a rate of 131.2 ppm of the racemate was required in order to provide 99.6% control.

The use of a single enantiomer of Imazalil against phytotoxic fungi has not previously been proposed. There has been no incentive and no recognized technological necessity for the use of the single enantiomer. Furthermore, it could not have been assumed, based on existing uses of Imazalil, that a reduction or complete elimination of the proportion of (R)-enantiomer in the racemate would solve the problem of delivering a maximally effective fungicide while ameliorating the unnecessary cost associated with the use of ineffective or marginally effective compounds. As yet, no (S)-enantiomer, or (S)-enantiomer-enriched racemates, of Imazalil have been made available for commercial use.

The invention therefore provides new methods of combating fungi which comprise applying to a plant, a seed of a plant, the locus of the plant or seed, or a fruit or grain or vegetable that has been harvested, a fungicidally effective amount of a compound of formula (I) or a composition containing the same. The compounds of the present invention can be used directly for agricultural purposes, but are more conveniently formulated into compositions using a carrier or diluent. The invention thus provides fungicidal compositions comprising a compound of formula (I) and an acceptable carrier or diluent therefor. In certain embodiments of the present invention, the compositions, including solid and liquid formulations, comprise 0.0001% to 20% by weight of the compound of formula (I). It is further preferred that the compositions comprise 0.001% to 2.0% of the compound of formula (I). It is still further preferred that the compositions of the present invention comprise 0.001% to 2.0%, more preferably 0.005% to 2.0% of a compound of formula (I).

The compositions of the present invention can be applied in a number of ways, including those well-known to persons skilled in the art. For example, the compositions can be applied formulated or unformulated, directly to the foliage of a plant, to seeds, to a medium in which plants are growing or are to be planted, or to fruits or vegetables after they have been harvested. The compositions can be sprayed on, dusted on, or applied as a cream or paste formulation, or they can be applied as a vapor or in granules, including slow release granules. The compositions can be applied to any part of the plant including the foliage, stems, branches or roots, or to soil surrounding the roots. Alternatively, the compositions can be applied to seeds before planting, or to soil, paddy water, or hydroponic culture systems. The compositions can also be injected into plants or sprayed onto vegetation using electrodynamic spraying techniques or other low volume methods, or applied by land or aerial irrigation systems.

When applied to the foliage of plants, compounds of the present invention can be applied, for example, at rates of from about 1.0 g to about 5 kg, preferably about 10 g to about 1 kg, more preferably about 20 g to about 0.4 kg, of active ingredient per hectare.

When used as seed dressings, the compounds of the present invention can be applied, for example, at rates from about 0.0001 g to about 10 g, preferably 0.005 g to 8 g, more preferably about 0.005 g to about 4 g, of active ingredient (i.e., compound of the invention of formula (I)) per kilogram of seed.

For use against phytotoxic fungi, the compositions of the present invention can be in the form of dustable powders or granules comprising active ingredient and a solid diluent or carrier, such as, for example, filler such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. Granules can be prepared, for example, by incorporating active ingredient into pellets of filler, or by treating pre-formed pellets of filler with active ingredient. Compositions for dressing seed can include an agent, such as, for example, a mineral oil, to improve the adhesion of the composition to seeds. Alternatively, the active ingredient can be formulated for seed dressing purposes using an organic solvent, such as, for example, N-methylpyrrolidone, propylene glycol or N,N-dimethylformamide. The compositions can be used in the form of water dispersible powders or water dispersible granules and can comprise wetting or dispersing agents to facilitate dispersion in liquids. The powders and granules can also contain fillers and suspending agents known to those skilled in the art.

The compositions of the present invention can be provided as soluble powders or granules, or as solutions in polar solvents. Soluble powders can be prepared by mixing the active ingredient with a water-soluble salt such as sodium bicarbonate, sodium carbonate, magnesium sulphate or a polysaccharide, and a wetting or dispersing agent to improve water dispersibility and/or solubility. The mixture can then be ground to a fine powder. Similar compositions can also be granulated to form water-soluble granules. Solutions can be prepared by dissolving the active ingredient in polar solvents such as ketones, alcohols and glycol ethers. Such solutions can, optionally, contain one or more surfactants to improve dissolution or suspension in aqueous media and prevent crystallization in a spray tank.

Emulsifiable concentrates or emulsions can be prepared by dissolving the total active ingredient in an organic solvent optionally containing a wetting or emulsifying agent, and then adding the mixture to water, which can optionally contain a wetting or emulsifying agent. Suitable organic solvents include aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of insoluble or poorly soluble solids can be prepared by ball or bead milling with a dispersing agent, with a suspending agent included to reduce settling of the solids. Compositions applied by spraying can be in the form of aerosols wherein the formulation is held in a container under pressure of a propellant. As a propellant, fluorotrichloromethane or dichlorodifluoromethane is suitable.

If desired, compositions of the present invention can be applied as a smoke by mixing the dry active ingredient with a pyrotechnic mixture to form a composition suitable for generating in enclosed spaces a smoke containing the compounds. As still another option, the compounds of the present invention can be used in micro-encapsulated form, or can be formulated in biodegradable polymeric formulations to obtain a slow, controlled release of the active substance.

By including suitable additives, such as, for example, additives for improving the uptake, distribution, adhesive power, and resistance to rain on treated surfaces, the different compositions can be better adapted for various utilities. Suitable additives known in the art can be included to improve the biological efficacy of the various formulations. Such additives can include surface active agents to improve wetting and retention on surfaces treated with the formulation, and also the uptake and mobility of the active material. Other optional additives include oil-based spray additives, for example, certain mineral oils and natural plant oils, such as, for example, soya bean and rape seed oil. These and other additives can be used in conjunction with other adjuvants.

The compounds of the present invention can be used in combination with fertilizers such as, for example, nitrogen-, potassium- or phosphorus-containing fertilizers. For example, compositions containing one or more fertilizers can be in the form of granules, and such granules can suitably contain up to about 25% by weight of active ingredient.

One skilled in the art will recognize that water dispersible powders, emulsifiable concentrates, and suspension concentrates can contain one or more surfactants, which can function as wetting agents, dispersing agents, emulsifying agents, and/or suspending agents. Such surfactants can be cationic, anionic, or non-ionic agents. Suitable cationic surfactants include quaternary ammonium compounds, such as, for example, cetyltrimethylammonium bromide. Suitable anionic surfactants include soaps, salts of aliphatic monoesters of sulphuric acid, such as, for example, sodium lauryl sulphate, and salts of sulphonated aromatic compounds, such as, for example, sodium dodecylbenzenesulphonate, sodium, calcium or ammonium lignosulphonate, butylnaphthalene sulphonate, or a mixture of sodium diisopropyl- and triisopropylnaphthalene sulphonates. Suitable non-ionic surfactants include the condensation products of ethylene oxide with fatty alcohols such as oleyl or cetyl alcohol, or with alkyl phenols such as octyl- or nonylphenol and octylcresol. Other suitable non-ionic agents include partial esters derived from long chain fatty acids and hexitol anhydrides, alkyl glucosides, polysaccharides, and lecithins, and the condensation products of the said partial esters with ethylene oxide. Suitable suspending agents include hydrophilic colloids such as polyvinylpyrrolidone and sodium carboxymethylcellulose, and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and, after such storage, be capable of dilution with water in order to form aqueous preparations which remain homogeneous for a sufficient time to enable them to be applied by conventional spray equipment. The concentrates can conveniently contain up to 95%, suitably 1–85%, for example 1–25% or 25–60%, by weight of the active ingredient. After dilution to form aqueous preparations, such preparations can contain varying amounts of the active ingredient depending upon the intended purpose, but an aqueous preparation containing 0.0001 to 20%, for example 0.001 to 2%, by weight of active ingredient can be used.

Compositions of the present invention comprising compounds of formula (I) can be mixed with soil, peat or other rooting media for the protection of plants against seed-borne, soil-borne or foliar fungal diseases.

The compositions of the present invention can contain other compounds having biological activity. Suitable biologically active compounds for use with the compounds of the present invention include those having similar or complementary fungicidal activity or having plant growth regulating, herbicidal or insecticidal activity. When additional fungicidal compounds are included in the compositions, the compositions can have a broader spectrum of activity or a greater level of intrinsic activity than compounds of formula (I) alone. In some cases, inclusion of one or more additional fungicides can have a synergistic effect on the fungicidal activity of compounds of formula (I). Additional fungicidal compounds suitable for use in compositions of the present invention include (R,S)-1- aminopropylphosphonic acid; (R,S)-4-(4-chlorophenyl)-2-phenyl-2-(1,2,4-triazol-1-ylmethyl)butyronitrile; (Z)-N-but-2-enyloxymethyl-2-chloro-2',6'-diethylacetanilide; 1-(2-cyano-2-methoxyiminoacetyl)-3-ethyl urea; 4-(2,2-difluoro-1,3-benzodioxol-4-yl)pyrrole-3-carbonitrile; 4-bromo-2-cyano-N,N-dimethyl-6-trifluoromethylbenzimidazole-1-sulphonamide; 5-ethyl-5,8-dihydro-8-oxo(1,3)-dioxol-(4,5-g)quinoline-7-carboxylic acid; alpha-[N-(3-chloro-2,6-xylyl)-2-methoxyacetamido]-gamma-butyrolactone; N-(2-methoxy-5-pyridyl)-cyclopropane carboxamide; alanycarb; aldimorph; ampropylfos, anilazine; azaconazole; BAS 490F; benalaxyl; benomyl; biloxazol; binapacryl; bitertanol; blasticidin S; bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper-containing compounds such as copper oxychloride, copper oxyquinolate, copper sulphate, copper tallate, and Bordeaux mixture; cyclohex-imide; cymoxanil; cyproconazole; cyprofuram; debacarb; di-2-pyridyl disulphide 1,1'-dioxide; dichlofluanid; dichlone; diclobutrazol; diclomezine; dicloran; didecyl dimethyl ammonium chloride; diethofencarb; difenoconazole; O,O-di-iso-propyl-5-benzyl thiophosphate; dimefluazole; dimetconazole; dimethomorph; dimethirimol; diniconazole; dinocap; dipyrithione; ditalimfos; dithianon; dodemorph; dodine; doguadine; edifenphos; epoxiconazole; etaconazole; ethirimol; ethoxyquin; ethyl(Z)-N-benzyl-N-([methyl (methyl-thioethylideneamino-oxycarbonyl) amino]thio)-beta-alaninate; etridiazole; fenaminosulph; fenapanil; fenarimol; fenbuconazole; fenfuram; fenpiclonil; fenpropidin; fenpropimorph; fentin acetate; fentin hydroxide; ferbam; ferimzone; fluazinam; fludioxonil; fluoroimide; fluquinconazole; flusilazole; flutolanil; flutriafol; folpet; fuberidazole; furalaxyl; furconazole-cis; guazatine; hexaconazole; hydroxyisoxazole; hymexazole; ICIA5504; imibenconazole; ipconazole; iprobenfos; iprodione; isopropanyl butyl carbamate; isoprothiolane; kasugamycin; mancozeb; maneb; mepanipyrim; mepronil; metalaxyl; metconazole; methfuroxam; metiram; metiram-zinc; metsulfovax; myclobutanil; neoasozin; nickel dimethyldithiocarbamate; nitrothia-iso-propyl; nuarimol; ofurace; organomercury compounds; oxadixyl; oxolinic acid; oxycarboxin; pefurazoate; penconazole; pencycuron; phenazin oxide; phosetyl-Al; phosphorus acids; phthalide; polyoxin D; polyram; probenazole; prochloraz; procymidone; propamocarb; propamocarb hydrochloride; propiconazole; propineb; propionic acid; prothiocarb; pyracarbolid; pyrazophos; pyrifenox; pyrimethanil; pyroquilon; pyroxyfur; pyrrolnitrin; quaternary ammonium compounds; quinconazole; quinomethionate; quintozene; rabenazole; sodium pentachlorophenate; streptomycin; sulphur; SSF-126; tebuconazole; techlofthalam; tecnazene; tetraconazole; thiabendazole; thicyofen; thifluzamide; 2-(thiocyanomethylthio)benzothiazole; thiophanate-methyl; thiram; timibenconazole; tolclofos-methyl; tolylfluanid; triacetate salt of 1,1'-iminodi (octamethylene)diguanidine; triadimefon; triadimenol; triazbutyl; triazoxide; tricyclazole; tridemorph; triforine; triflumizole; triticonazole; validamycin A; vapam; vinclozolin; XRD-563; zineb; and ziram.

The following examples are merely illustrative of the present invention and should not be considered limiting of the scope of the invention in any way. These examples, and equivalents thereof, will become more apparent to those skilled in the art in light of the present disclosure and the accompanying claims.

EXAMPLES

Example 1

Synthesis of Racemic Imazalil

2-Bromo-2',4'-dichloroacetophenone: 25 g (0.1322 mol) of 2',4'-dichloroacetophenone was placed in a three-neck round bottom flask equipped with a magnetic stir bar, reflux condenser, and dropping funnel. Anhydrous ether (30 mL) and AlCl$_3$ (0.20 g) were added. The solution was stoppered and cooled to 0° C. in an ice bath. Br$_2$ (21.13 g, 0.1322 mol) was added dropwise (at a rate of approximately 0.5 mL/min). After addition of Br$_2$ was complete, HBr and the solvent were removed under reduced pressure. The remaining HBr was removed by blowing a stream of nitrogen over the orange oily product. The resulting oil was placed under high vacuum until all the bubbling had ceased. The product was obtained as a viscous orange oil, which solidified upon standing in the refrigerator. Yield: 35.72 g (100%); TLC: 95% Hexanes/5% Acetone, R$_f$=0.35.

2-(1H-Imidazole)-2',4'-dichloroacetophenone: 2-Bromo-2',4'-dichloroacetophenone (35.72 g; 0.1322 mol) was dissolved in 250 mL of anhydrous ether. This solution was filtered into a 1-liter round bottom flask to remove insoluble aluminum salts remaining from the bromination reaction. Imidazole (17.70 g, 0.26 mol) was added, and the solution stirred, at room temperature, for 4 hours. At the end of 4 hours, an insoluble orange oil had formed at the bottom of the flask. Ethanol (85 mL) was added, and the solution stirred overnight. The solution was filtered to remove a pinkish solid by-product that was washed with a small amount of ether and dried (5.50 g). The combined washings and filtrate were treated with 400 mL of 10% NaOH. The phases were separated and the aqueous phase extracted with 150 mL of ether. The organic phases were combined. The combined ether layers were cooled in the freezer overnight, and the resultant solid, which was obtained by filtration, was washed with anhydrous ether and dried. Yield: 13.50 g (40%); m.p. 61–64° C.

1-(2',4'-Dichlorophenyl)-2-(1H-imidazole)-1-ethanol:

(a) 2-(1H-imidazole)-2',4'-dichloroacetophenone (8 g, 31.36 mmol) and methanol (100 mL) were placed in a 250 mL round bottom flask equipped with a magnetic stir bar. NaBH$_4$ (1.20 g, 31.72 mmol) was added, and the solution stirred for 45 minutes at room temperature. An additional 0.30 g of NaBH$_4$ was added, and the solution stirred for an additional 3 hours. The resulting solution was partitioned between ether and water (300 mL, 1:1), and the ether layer was separated and placed in a freezer overnight. The resulting crystals were obtained by filtration, and washed with anhydrous ether. The product was then dried under reduced pressure, and obtained as a white solid. Yield: 7 g (87%); m.p. 129–132° C.

(b) An alternative method for the preparation of 1-(2',4'dichlorophenyl)2-(1H-imidazole)-1-ethanol follows. Four g (17.74 mmol) of (±)-2-chloro-(2',4'dichlorophenyl)-1-ethanol, prepared by sodium borohydride reduction of 2,2',4'-trichloroacetophenone (purchased from Aldrich Chemical), and 5.00 g (73.44 mmol) of imidazole were dissolved in 15 mL of dry 2-butanone in a 100 mL round bottom flask equipped with a magnetic stirrer bar and reflux condenser. Four g K$_2$CO$_3$ and a catalytic amount of NaI were added and the solution was refluxed under a nitrogen atmosphere for 36 hours. After cooling to room temperature, the reaction mixture was filtered. Ether was added to the filtrate and the resulting solution was washed with 50 mL of water and the layers separated. The aqueous layer was extracted 3 times with 50 mL portions of ether. The ether extracts were combined with the previous organic phase and the total dried over anhydrous MgSO$_4$. After filtration to remove MgSO$_4$, the filtrate was concentrated to give a yellowish oil. Chromatography of the crude product (CH$_2$Cl$_2$:CH$_3$OH/95:5) provided 3.59 g of purified pale yellow crystals (78.7% yield).

1-(β-Allyloxy-β-2',4'-dichlorophenylethyl)imidazole (Imazalil):

(a) 1-(2',4'-dichlorophenyl)-2-(1H-imidazole)-1-ethanol (5 g, 19.45 mmol) was dissolved in 83 mL of anhydrous THF in a 250 mL round bottom flask equipped with a magnetic stir bar, and sealed with a rubber septum. The flask was flushed with nitrogen, and NaH (0.52 g, 21.67 mmol) was added. The flask was immediately stoppered with the rubber septum. A needle connected to a gas outlet tube was introduced into the flask via the septum, to enable removal of hydrogen. After about 30 minutes, when the evolution of hydrogen had subsided, 2.10 mL (2.94 g, 24.3 mmol) of allyl bromide was added slowly to the stirring solution, via a syringe. The solution was allowed to stir overnight at room temperature, then poured into 100 mL of water and extracted with ether. The orange ether layer was washed with an additional 100 mL of water and separated. The ether layer was dried over anhydrous MgSO$_4$, filtered, and evaporated to yield Imazalil free base as a viscous golden oil. Yield: 5 g (87%); TLC: Acetone, R$_f$=0.50.

(b) An alternative method for preparation of (±)-1-(β-allyoxy-β-(2',4'-dichlorophenylethyl))imidazole follows. 0.17 g (0.66 mmol.) of (±)-α-(2',4'-dichlorophenyl)-1H-imidazole-1-ethanol was dissolved in 7 mL of dry dioxane in a 25 mL round bottom flask. Sodium hydride (0.1 g; 4.2 mmol) and 0.1 g NaCl was added into the solution with stirring in a nitrogen atmosphere. The mixture was warmed to 35° C. and 0.5 mL of allyl chloride was added. After an additional 5 min., the mixture was heated to 50° C. and 0.5 mL more of allyl chloride added. The course of reaction was monitored by TLC and when complete, the mixture was cooled and then quenched with water. The entire contents were extracted 3 times with 100 mL portions of ether, the combined ether extracts were washed with saturated NaHCO$_3$ solution and the organic layer dried over anhydrous MgSO$_4$. After removal of drying agent and concentration of the filtrate, a crude yellowish oily product was obtained. After chromatography (CH$_2$Cl$_2$:CH$_3$OH/95:5) (±)imazalil (0.159 g) was obtained as a pale brownish viscous oil that solidified in time; yield: 81%.

Example 2

Synthesis of (R)-(-)-Imazalil (R)-2-Chloro-(2',4'-dichlorophenyl)-1-ethanol: To a solution containing 16 g (49.90 mmol) of (-)-DIP-Cl in 30 mL of anhydrous THF, at -25° C. (dry ice, CCl$_4$), under nitrogen, was added 10 g (44.74 mmol) of 2,2',4'-trichloroacetophenone. The stoppered solution was stirred at -25° C. for about 7 hours, and then at room temperature overnight. THF was removed in vacuo, and (+)-α-pinene was removed under high vacuum at room temperature overnight. The resulting viscous colorless oil was dissolved in 200 mL of anhydrous ether, and cooled to 0° C. Diethanolamine (10.50 g, 0.10 mol) was added to the filtrate, and stirring was continued for 3 hours at room temperature. The white solid obtained was removed by filtration and washed with anhydrous ether. The colorless solution was evaporated to dryness to yield a viscous colorless oil. This oil was flash chromatographed on silica gel, first with hexanes to remove (+)-α-pinene. The product was eluted from the column with 93% hexanes/7% acetone to yield 11.30 g of a white solid. This solid was crystallized from hexanes at 0° C. Yield: 5.75 g (57%); TLC: 95% hexanes/5% acetone, R$_f$=0.10.

(R)-2-Iodo-(2',4'-dichlorophenyl)-1-ethanol: (R)-2-Chloro-(2',4'-dichlorophenyl)-1-ethanol (1.95 g, 8.65 mmol) was dissolved in 60 mL of anhydrous acetone (4A molecular sieves). Then NaI (7 g, 46.70 mmol) was added to the solution and the solution refluxed for 3 hours under nitrogen. Upon cooling to room temperature, the solution was poured into 160 mL of hexanes/ethyl acetate (3:1), and filtered to remove excess NaI which had precipitated. The filtrate was evaporated to dryness in vacuo, and the residue treated with ether and decanted from the solid NaI. Upon removal of ether, the product was obtained as white solid. Yield: 2.40 g (88%).

(R)-α-(2',4'-dichlorophenyl)-1H-imidazole-1-ethanol:

(a) 2.40 g (7.57 mmol) of (R)-2-iodo-(2',4'-dichlorophenyl)-1-ethanol was treated with about 6 mL of triethylamine and imidazole (2.50 g, 36.7 mmol). The solution was heated under nitrogen, with the flow of nitrogen rapid enough to enable triethylamine to evaporate from the reaction mixture. When almost all the triethylamine has evaporated, the reaction mixture was heated at 95–100° C. for about 6 hours. Upon cooling, the yellow viscous residue was partitioned between water and ether. The ether layer was separated from the aqueous layer, and the ether layer was washed with water. The ether layer was then evaporated to dryness, and the resulting residue was placed under high vacuum to remove any remaining volatiles. The product was obtained as a highly viscous, yellow oil. Yield: 1.61 g (83%); $[α]_D^{22}$=-67.7° (c=16.1, MeOH).

(b) The preparation of the (R)-enantiomer also can be accomplished from (R)-2-chloro-(2',4'dichlorophenyl)-1-ethanol using an analogous mehtodology (b) to that described for the racemic form of the comparable material in Example 1.

(R)-(-)-1-(β-allyloxy-β-2',4'-dichlorophenylethyl)imidazole:

(a) 2.05 g (7.97 mmol) of (R)-α-(2',4'-dichlorophenyl)-1H-imidazole-1-ethanol was dissolved in 40 mL of anhydrous THF in a 250 mL round bottom flask equipped with a magnetic stir bar and sealed with a rubber septum. The solution was flushed with nitrogen, and 0.21 g (8.75 mmol) of NaH was added to the stirring solution. After 30 minutes at room temperature under nitrogen, 1.10 g (9.09 mmol) of allyl bromide was added to the stirring solution. The stoppered solution was stirred at room temperature for 24 hours. Next, 120 mL of water was added, and the solution was extracted with ether. The ether layer was washed with saturated brine, dried over anhydrous MgSO$_4$, filtered, and evaporated to give 1.96 g of crude (R)-(-)-Imazalil as a viscous golden oil (crude yield: 83%). This oil was dissolved in about 30 mL of ether, and 0.65 g (6.63 mmol) of H$_2$SO$_4$ in 5 mL of water was added to the stirring solution. The solvent was removed in vacuo to give 2.61 g of a highly viscous, reddish oil. The sulfate salt was chromatographed on silica gel, first eluting with acetone, then with acetone/methanol (2:1), to yield 1.90 g of the salt. $[α]_D^{23}$=-56.6° (c=7.6, MeOH). The salt was converted to its free base form, and was purified by silica gel chromatography, yielding 0.95 g of (R)-(-)-Imazalil. $[α]_D^{22}$=-77.9° (c=9.5, MeOH).

(b) The (R)-(-)-enantiomer can also be obtained from (R)-α-(2',4'-dichlorophenyl)-1H-imidazole-1-ethanol in a manner analogous to that described in procedure (b) for the racemic material in Example 1.

Example 3

Synthesis of (S)-(+)-Imazalil (S)-2-Chloro-(2',4'-dichlorophenyl)-1-ethanol: To a solution containing 16 g (49.90 mmol) of (+)-DIP-Cl in 30 mL of anhydrous THF, at -25° C. (dry ice, CCl$_4$), under nitrogen, was added, in portions, 10 g (44.74 mmol) of 2,2',4'-trichloroacetophenone. The stoppered solution was stirred at −25° C. for about 7 hours, and then for two days at room temperature under nitrogen. 100 mL of 10% HCl was added, and the solution was extracted with ether. The ether layer was washed with 100 mL of water, and then concentrated in vacuo. The resulting colorless oil was placed under high vacuum for 7 hours, with stirring, to remove (−)-α-pinene. The oil was taken up into 250 mL of ether and cooled to 0° C. Diethanolamine (10.50 g, 0.10 mol) was added to the solution and stirring continued for 10 minutes at 0° C. The ice bath was removed and the solution stirred at room temperature for 2.5 hours. The solution was filtered, and the solid washed with ether. Upon removal of the ether, 15.50 g of a slightly viscous, yellow oil was obtained. This oil was chromatographed on silica gel, eluting first with hexanes to remove the α-pinene, and then with hexanes/acetone (93%/7%) to elute the product alcohol as a white solid. The solid was crystallized from hexanes, at 0° C., to give pure halohydrin as a white crystalline solid in the form of needles. Yield: 4.80 g (43%).

(S)-2-Iodo-(2',4'-dichlorophenyl)-1-ethanol: (S)-2-Chloro-(2',4'-dichlorophenyl)-1-ethanol (4 g, 17.74 mmol) was dissolved in 100 mL of anhydrous acetone (4 Å molecular sieves). The solution was flushed with nitrogen, and NaI (12.75 g, 85.10 mmol) was added to the solution and the solution refluxed for 3.5 hours under nitrogen. Upon cooling to room temperature, the solution was poured into about 320 mL of hexanes/ethyl acetate (3:1), with stirring. The solution was then filtered to remove excess NaI which had precipitated. The filtrate was evaporated to dryness in vacuo to yield a yellow oil. The oil was decanted, the residue treated with ether, and the ether washings decanted from the solid NaI. The ether solutions were combined and evaporated to dryness. Upon removal of ether, the product was obtained as a yellow crystalline solid. Yield: 4.70 g (84%).

(S)-α-(2',4'-dichlorophenyl)-1H-imidazole-1-ethanol:

(a) 4.70 g (14.83 mmol) of (S)-2iodo-(2',4'-dichlorophenyl)-1ethanol and 5 g (73.44 mmol) of imidazole were added to 11 mL of triethylamine. The solution was refluxed under nitrogen, with the flow of nitrogen rapid enough to enable triethylamine to evaporate from the reaction mixture. When almost all the triethylamine has evaporated, the reaction mixture was heated at 95–100° C. for about 8hours, under nitrogen. The cooled solution was partitioned between ether and water, and the aqueous layer was removed. The ether layer was washed with water and separated. The ether layer was then evaporated to dryness, and the resulting residue was dissolved in 40 mL of methanol. The methanol was removed in vacuo, and the product was obtained as a highly viscous, slightly yellow oil. Yield: 3.50 g (92%); $[\alpha]_D^{22}$=+68.6° (c=14, MeOH).

(b) The preparation of the (S) enantiomer also can be accomplished from (S)-α-chloro-(2',4'-dichlorophenyl)-1-ethanol using a procedure analogous to methodology (b) described for the racemic form of the material in Example 1.

(S)-(+)-1-(β-Allyloxy-β)-2',4'-dichlorophenylethyl)imidazole:

(a) 2.93 g (11.40 mmol) of (S)-α-(2',4'-dichlorophenyl)-1-imidazole-1-ethanol was dissolved in 50 mL of anhydrous THF in a 250 mL round bottom flask equipped with a magnetic stir bar and sealed with a rubber septum. The solution was flushed with nitrogen, and 0.30 g (12.50 mmol) of NaH was added to the stirring solution under nitrogen. After 30 minutes at room temperature under nitrogen , 1 mL (15.56 mmol) of allyl bromide was added to the stirring solution. The stoppered solution was stirred at room temperature for 24 hours. Next, about 120 mL of water was added, and the solution was extracted with ether. The ether layer was washed with saturated brine, dried over anhydrous MgSO$_4$, filtered, and evaporated to give 2.55 g of crude (S)-(+)-Imazalil as a viscous golden oil (crude yield: 75 %). $[\alpha]_D^{22}$=+69.6° (c=10.2, MeOH). To this oil was added 12 mL of water, and then 0.84 g (8.58 mmol) of H$_2$SO$_4$ in 5 mL of water was added to the stirring solution. The water was then removed under high vacuum and gentle heat. The residue was chromatographed on silica gel, first eluting with acetone to remove less polar impurities, then with acetone/methanol (3:1), to yield 2.30 g of the sulfate salt as a slightly yellow semi-solid. $[\alpha]_D^{22}$=+59.8° (c=9.2, MeOH). The salt was converted to its free base form, and was purified by silica gel chromatography, yielding 1.37 g of (S)-(+)-Imazalil. $[\alpha]_D^{22}$=+81.0° (c=13.7, MeOH).

(b) The (S)-(+) enantiomer also can be obtained from (S)-α-(2',4'-dichlorophenyl)-1H-imidazole-1-ethanol in a manner analogous to that described in procedure (b) in Example 1 for the comparable racemic material.

Example 4

Chiral GC Analysis of Halohydrin Intermediates Prepared During the Synthesis of Imazalil A 15 mg sample of the pure halohydrin intermediate was dissolved in 400 μL of anhydrous THF containing 5 drops of anhydrous pyridine, in a Reacti-Vial. To this solution was added 20 mg of (R)-(−)-α-methoxy-α-trifluoromethylphenylacetyl chloride, and the solution was stirred. A copious precipitate of pyridinium hydrochloride was formed almost immediately. The solution was allowed to stand at room temperature overnight. 10% NaOH (1 mL) was added to the solution, and the solution was extracted with ether. The aqueous phase was discarded and the organic phase (ether layer) was washed with water. The ether layer was concentrated, yielding about 30 mg of a highly viscous, colorless oil. This oil was dissolved in methanol, diluted to 50 mL with water, and used for subsequent GC analysis. GC Column: Supelcowax 10 fused-silica capillary column, 15 m, 0.53 mm I.D., 1.0 μM;

Conditions: 200° C. isothermal; Retention times of product diastereomeric esters: (R,R)=16.93 min., (S,R)=15.42 min.

A Mosher's Acid blank (above procedure without the halohydrin) was injected under the above conditions. No peak was observed in the chromatogram. The underivatized halohydrin was found to have a retention time of 3.66 minutes. The (R)-enantiomer of the halohydrin was determined to have an ee of 99.0%, and the (S)-enantiomer was found to have an ee of at least 99.9% with no integratable amount of the (R)-enantiomer being detected. The values for the optical purity of the se halohydrins were in agreement with those reported in the literature. Brown et al., *J. Org. Chem.*, 1988, 53, 2916.

Example 5

Efficacy of (R)-1-[2-(2,4-dichlorophenyl)-2-(propenyloxy)ethyl]-1H-imidazole (Imazalil) Against *Aspergillus nidulans*

Solutions of racemic Imazalil and single enantiomers in acetone were made according to standard dilution procedures. Each solution was spotted in 5 microliter (μL) aliquots onto the center of 10 cm potato dextrose agarplates previously treated with an inoculum of *Aspergillus nidulans*. In untreated plates (controls), the innoculum developed into a fungal mata within 3 days. Where inhibitory levels of fungicide had been introduced, inhibition zones were observed, the size of which depended upon the concentration and identity of the fungicidal compound (i.e., racemate or single enantiomer) applied. Results are shown in Table 1.

TABLE 1

Inhibition zone diameter (cm)

| Isomer | 50 µg | 5 µg | 0.5 µg | 0.05 µg | 0.005 µg |
|---|---|---|---|---|---|
| (R, S) | 6.0–6.5 | 3.5–4.0 | 2.0–2.5 | 0 | 0 |
| (R) | 4.0–4.5 | 2.5–3.0 | 1.0–1.5 | 0 | 0 |
| (S) | 6.0–6.5 | 4.0 | 2.5–3.0 | 0 | 0 |

As indicated by the sizes of the inhibition zones, the (S)-enantiomer was as effective at a given concentration as was the (R)-enantiomer at ten times the same concentration.

Example 6
Efficacy of Racemate and Single Enantiomers of 1-[2,4-dichlorophenyl)-2-(propenyloxy)ethyl]-1H-imidazole Against Powdery Mildew (*Erysiphe graminis*) on Wheat Plants Compounds to be tested were formulated in a mixture of 5% acetone and 0.25% Triton X-155™ surfactant in water at concentrations listed in Table 2. Wheat plants were sprayed with the test compounds at the indicated concentrations, applied with a hand-held sprayer and allowed to run off. Three plants were sprayed at each concentration. The plants were allowed to dry for 2 hours and then innoculated with fungus *Erysiphe graminis* f.sp. *graminis* by spraying the plants with a suspension of propagules of the fungus. Innoculated plants were incubated under conditions conducive to the growth of the fungus. Unsprayed, innoculated plants were included as controls to check for uncontrolled development of fungal disease.

When symptoms of fungal disease developed, percentage disease control was determined on treated plants. Percentage of diseased tissue on control plants was also determined. Disease control was estimated on a scale of 0–100%. Results are presented in Table 2. Diseased tissue on untreated, control plants was approximately 90% of total plant tissue.

ED50 (estimated concentration required to produce 50% killing of fungi) and ED90 (estimated concentration required to produce 90% killing of fungi) were also determined, and are presented in Table 3.

TABLE 2

Control of Powdery Mildew by racemate and single enantiomers

| Compound | Application rate, ppm | Percent control |
|---|---|---|
| (R)-enantiomer | 116 | 80 |
|  | 58 | 23.3 |
|  | 29 | 0 |
|  | 14.5 | 0 |
|  | 7.25 | 0 |
| Racemate | 131.2 | 99.6 |
|  | 65.6 | 98.6 |
|  | 32.8 | 73.3 |
|  | 16.4 | 60 |
|  | 8.2 | 40 |
| (S)-enantiomer | 153.6 | 100 |
|  | 76.8 | 99.3 |
|  | 38.4 | 86.6 |
|  | 19.2 | 60 |
|  | 9.6 | 26.6 |

TABLE 3

Efficacy of Single Isomers and Racemate Against Plant Pathogens

|  |  | Pi | Po | Bc | Eg | Pr |
|---|---|---|---|---|---|---|
| (R)-isomer |  |  |  |  |  |  |
|  | ED50(ppm) | 50 | 8 | 43 | 81 | 39 |
|  | ED90(ppm) | 407 | 70 | 72 | 137 | 109 |
| Racemate |  |  |  |  |  |  |
|  | ED50(ppm) | 31 | 14 | 38 | 12 | 17 |
|  | ED90(ppm) | 149 | 44 | 65 | 47 | 34 |
| (S)-isomer |  |  |  |  |  |  |
|  | ED50(ppm) | 21 | 6 | 42 | 16 | 17 |
|  | ED90(ppm) | 166 | 50 | 93 | 41 | 31 |

Key:
Pi  *Phytophthora infestans* (late blight); tested on: Tomato
Po  *Pyricularia oryzae* (Rice blast); tested on: Rice
Bc  *Botrytis cineria* (Gray mold); tested on: Pepper
Eg  *Erysiphe graminis* (Powdery mildew); tested on: Wheat
Pr  *Puccinia recondita* (Leaf rust): tested on: Wheat The results show that the (S)-enantiomer can be more effective than the racemate or the (R)-isomer. Various modifications of the invention, in addition to those described herein, will be apparent to those skilled in the art from the foregoing description. Such modifications are intended to fall within the scope of the appended claims.

What is claimed is:

1. A method for inhibiting the growth of fungus in association with a plant comprising applying to the locus of a plant a fungicidally effective amount of the (S)-enantiomer of 1-[2-(2,4-dichlorophenyl)-2-(2-propenyloxy)ethyl]-1H-imidazole, substantially free of the (R)-enantiomer.

2. The method of claim 1 wherein said fungus is Apergillus, *Erysiphe graminis*, Penicillium, Gloeosporium, Phomopsis, Fusarium, or Phoma.

3. The method of claim 1 wherein said plant is a fruit, vegetable or ornamental plant.

4. The method of claim 3 wherein said plant is a fruit or vegetable.

5. The method of claim 1 wherein said plant is a grass.

6. The method of claim 5 wherein said grass is a grain.

7. The method of claim 1 wherein said plant is a seed.

8. A fungicidal composition comprising a fungicidally effective amount of the (S)-enantiomer of 1-[2-(2,4-dichlorophenyl)-2-(2-propenyloxy)ethyl]-1H-imidazole, substantially free of the (R)-enantiomer, and an agriculturally acceptable carrier.

9. A fungicidal composition comprising a fungicidally effective amount of 1-[2-(2,4-dichlorophenyl)-2-(2-propenyloxy)ethyl]-1H-imidazole enriched in the (S) enantiomer wherein the enrichment is at least 70 mol percent.

10. A fungicidal composition comprising a fungicidally effective amount of 1-[2-(2,4-dichlorophenyl)-2-(2-propenyloxy)ethyl]-1H-imidazole, said imidazole being enriched in the (S) enantiomer, wherein the enrichment is at least 70 mol percent and an agriculturally acceptable carrier.

11. The composition of claim 10 wherein said enrichment is at least about 75 mol percent.

* * * * *